US008338177B2

(12) United States Patent
Mainwaring et al.

(10) Patent No.: US 8,338,177 B2
(45) Date of Patent: Dec. 25, 2012

(54) CELL CULTURE MEDIUM

(75) Inventors: David Mainwaring, Slough (GB);
Jeremy Wayte, Buckinghamshire (GB)

(73) Assignee: Lonza Biologics PLC, Slough, Berkshire (GB)

( * ) Notice: Subject to any disclaimer, the term of this patent is extended or adjusted under 35 U.S.C. 154(b) by 243 days.

(21) Appl. No.: 11/822,482

(22) Filed: Jul. 6, 2007

(65) Prior Publication Data

US 2008/0003679 A1 Jan. 3, 2008

Related U.S. Application Data

(62) Division of application No. 10/510,280, filed as application No. PCT/EP03/03631 on Apr. 8, 2003, now Pat. No. 7,258,998.

(60) Provisional application No. 60/411,751, filed on Sep. 19, 2002.

(30) Foreign Application Priority Data

Apr. 8, 2002 (GB) .................................. 0208041.4

(51) Int. Cl.
*C12N 5/06* (2006.01)
*C12P 21/06* (2006.01)
*C12N 9/10* (2006.01)
*C12N 5/00* (2006.01)
*C12N 0/071* (2006.01)

(52) U.S. Cl. ....... 435/404; 435/69.1; 435/193; 435/325; 435/372

(58) Field of Classification Search ................. 435/69.1, 435/193, 325, 372, 404
See application file for complete search history.

(56) References Cited

U.S. PATENT DOCUMENTS

| | | | |
|---|---|---|---|
| 4,216,203 A | | 8/1980 | Johnston |
| 4,767,704 A * | | 8/1988 | Cleveland et al. ............ 435/70.2 |
| 4,786,599 A * | | 11/1988 | Chessebeuf et al. .......... 435/381 |
| 5,030,564 A * | | 7/1991 | Mitsuhashi et al. ..... 530/388.23 |
| 5,045,468 A * | | 9/1991 | Darfler .......................... 435/395 |
| 5,266,479 A | | 11/1993 | Morris et al. |
| 5,378,612 A | | 1/1995 | Nakashima et al. |
| 5,422,274 A | | 6/1995 | Maddon et al. |
| 5,631,159 A * | | 5/1997 | Marshall et al. ............... 435/383 |
| 5,747,308 A | | 5/1998 | Bebbington et al. |
| 5,817,790 A | | 10/1998 | Tsuchiya et al. |
| 5,891,693 A | | 4/1999 | Bebbington et al. |
| 6,037,174 A * | | 3/2000 | Smith et al. .................... 435/366 |
| 6,048,728 A * | | 4/2000 | Inlow et al. .................... 435/404 |
| 6,103,529 A * | | 8/2000 | Price et al. ..................... 435/404 |
| 6,110,707 A | | 8/2000 | Newgard et al. |
| 6,395,484 B1 | | 5/2002 | Brandt et al. |
| 6,767,741 B1 * | | 7/2004 | Epstein et al. ................. 435/404 |
| 6,949,381 B2 | | 9/2005 | Baur et al. |
| 7,258,998 B2 * | | 8/2007 | Mainwaring et al. ......... 435/69.1 |
| 2002/0031825 A1 * | | 3/2002 | Bertheussen ................. 435/404 |

FOREIGN PATENT DOCUMENTS

| | | |
|---|---|---|
| CA | 2 234 118 | 7/1997 |
| EP | 0 239 292 A | 9/1987 |
| EP | 0 239 292 B1 | 9/1993 |
| WO | WO 98/24883 A2 | 6/1998 |

OTHER PUBLICATIONS

Japanese PCT National Publication No. 1988-503273 (corresponds to EP 0 239 292 cited in IDS filed Jul. 6, 2007).
WO87/05626 (corresponds to EP 0 239 292 cited in IDS filed Jul. 6, 2007).
Letter from Suzuye & Suzuye to Lonza Ltd. dated Sep. 26, 2008, issued in connection with Japanese Patent Application No. 2003-564226.
Letter from Suzuye & Suzuye to Lonza Ltd. dated Nov. 6, 2008, issued in connection with Japanese Patent Application No. 2003-564226 and English translation of Japanese Office Action mailed Sep. 24, 2008.
Kim et al, Biotechnology and Bioengineering, 2000-2001, vol. 71, No. 3, 2000, pp. 184-193.
U.S. Appl. No. 10/510,280, filed Nov. 2004, Mainwaring et al.
Kim et al, Biotechnology & Bioengineering, 2001, vol. 71, pp. 184-193.
Murakami et al, PNAS, 1982, vol. 79, pp. 1158-1162.
Zhang et al, Chinese Journal of Biotechnology, 1999, vol. 14, No. 3, pp. 187-193.
Whitford, Bioprocess International, Dec. 2003, pp. 36-44.
Canadian Office Action dated Sep. 28, 2009, issued in connection with Canadian Patent Application No. 2,480,126.
Galfre et al, "Preparation of Monoclonal Antibodies: Strategies and Procedures", Methods in Enzymology, vol. 73, pp. 3-46 (1981).
Office Action dated Oct. 28, 2010, issued in connection with U.S. Appl. No. 90/011,025, (Reexam of U.S. Patent No. 7,258,998).
Alkanoic Acids, SavitalPall.com, pp. 1-11, printed Oct. 21, 2010.
Huheey et al, "Principles of Structure and Reactivity", Inorganic Chemistry, pp. 27-28, Fourth Edition, (Jane Piro ed., Harper Collins College Publishers) (1993).
RPMI-1640 Media Product Information, "Biochemicals and Reagents for Life Science Research ", Sigma 2000/2001 Catalog, 4 pages.
Ege, "Structure and Reactivity", Organic Chemistry, Third Edition, pp. 583-584, (Hamann K. P. et al. ed., D.C Health and Company) (1994).
Ex Parte Reexamination Communication (Order Granting/Denying Request for Ex Parte Reexamination) dated Jul. 1, 2010, issued in connection with U.S. Appl. No. 90/011,025.

(Continued)

*Primary Examiner* — Herbert J Lilling
(74) *Attorney, Agent, or Firm* — Nixon & Vanderhye P.C.

(57) ABSTRACT

A method for culturing cells in the presence of an alcanoic acid for enhancing protein production.

15 Claims, 16 Drawing Sheets

OTHER PUBLICATIONS

Office Action dated Apr. 27, 2011, issued in connection with U.S. Re-Examination U.S. Appl. No. 90/011,025.
Office Action dated Jul. 21, 2011, issued in connection with U.S. Re-Examination U.S. Appl. No. 90/011,025.
Amendment filed Dec. 23, 2010, in connection with U.S. Re-Examination U.S. Appl. No. 90/011,025.
Appeal Brief filed Oct. 17, 2011, in connection with U.S. Re-Examination U.S. Appl. No. 90/011,025.

\* cited by examiner

| Parameter | Control | Potassium acetate (mM) | | | Sodium acetate (10 mM) |
|---|---|---|---|---|---|
| | | 5 | 10 | 15 | |
| CCT ($10^6$ cell h $mL^{-1}$) | 554 | 597 (8%) | 593 (7%) | 572* (3%) | 535 (-3%) |
| Product (mg $L^{-1}$) | 365 | 448 (23%) | 480 (32%) | 487* (33%) | 501 (37%) |
| $q_P$ (mg $10^6$ cells$^{-1}$ h$^{-1}$) | 0.659 | 0.752 (14%) | 0.810 (23%) | 0.852 (29%) | 0.937 (42%) |

- *A duplicate culture exhibited very poor cell growth. No product concentration was determined.

Fig. 1

| Treatment | Maximum viable cell concentration | CCT | Product concentration | $q_P$ |
|---|---|---|---|---|
| No acetate (Control) | 0% | 0% | 0% | 0% |
| 5mM in inoculum | -4% | 23% | 24% | 12% |
| 10mM in inoculum | 24% | 40% | 97% | 56% |
| 5mM at feed | 8% | -13% | -15% | -5% |
| 10mM at feed | 1% | -8% | 8% | 17% |
| 15mM at feed | 26% | 7% | 1% | -3% |
| 5mM in inoc - 10mM at inoc | 9% | 59% | 98% | 39% |
| 5mM in inoc - 10mM at feed | 12% | 47% | 73% | 28% |

Fig. 4

CELL CULTURE MEDIUM

The present application is a divisional of U.S. application Ser. No. 10/510,280, filed Nov. 24, 2004 (issued as U.S. Pat. No. 7,258,998), which is a U.S. national phase of international application PCT/EP03/03631, filed 8 Apr. 2003, which designated the U.S. and claims benefit of GB Application No. 0208041.4, filed 8 Apr. 2002 and U.S. Provisional Application Ser. No. 60/411,751, filed 19 Sep. 2002, the entire contents of each of which is hereby incorporated by reference in this application.

The present invention relates generally to the field of animal cell culture. It devises a method of culturing animal cell for production of therapeutic or other useful proteins and a respective cell culture medium.

Sodium butyrate or other salts of butyric acid are well-known to enhance yield of protein produced in animal cell culture as is described e.g. in EP-239 292 A. The effect can be observed for naturally secreted proteins, e.g. antibodies from hybridomas, or recombinant cell lines. Butyrate is added to cell culture medium in a concentration of preferably up to 5 mM. The effect of butyric acid is rather specific as is confirmed by a wealth of scientific literature on addition of butyric acid to culture medium; propionate or pentanoate are considerably less effective at concentrations at about 1 mM.

However, there are limitations and backdraws to the use of butyrate as a cell culture supplement. Addition of butyrate in the 0.1-10 mM range needs to be carefully balanced in order to avoid overdosing and the ensuing toxic and cytostatic effects. The negative effect on growth rate can be drastic even upon minor increases in concentration. For each cell line and recombinant clone, the optimal amount of butyrate has to be carefully chosen and controlled during large scale bioreactor cultivation. E.g., according to EP-239 292 A, for hybridoma cells a concentration range of from 0.1 mM to 1 mM is recommended, whereas other cell lines may well tolerate butyrate at concentrations beyond 1 mM. It is well-known that hybridoma cells are much more sensitive for adverse effects of e.g. insufficient oxygen or nutrient supply or toxic influences of chemical compounds than are other cell types, and that they will easily and irreversibly start programmed cell death once having received such negative stimulus. In as much, butyrate has proven to be a somewhat Janus-faced means for increasing productivity in cell culture.

Kim et al. (Biotechnology and Bioengineering 71, 2001, 184-193, Overexpression of bcl-2 inhibits sodium butyrate-induced apoptosis in CHO cells resulting in enhanced humanized antibody production) countered the cytotoxic effect of sodium butyrate at 5 mM by means of bcl-2 recombinant cell lines which measure resulted in enhanced protein production. However, this method requires extensive cell line engineering for creating recombinants producing both rekombinant bcl-2 and a product protein. A more simple method to counter the negative effects of butyrate medium supplements would be advantageous.

U.S. Pat. No. 5,378,612 describes a synergistic, protein yield enhancing effect of adding lithium salts (10 mM) or lipopolysaccharide (LPS, 1 μg/ml) to a culture medium for CHO cell culture already comprising sodium butyrate at 1 mM. For two different lithium salts, the yield effect was in the order of 1.3 times, whereas LPS showed an enhancing effect of about 4 times in comparison to the butyrate control. Interestingly, sodium acetate at 10 mM proved to be of literally no benefit over the control in this test system.

Kooistra et al. (Biochem. J. 1987, Butyrate stimulates tissue-type plasminogen-activator synthesis in cultured human endothelial cells, 247:605-612) tested in serum-containing, endothelial cell culture various compounds on their potentially expression-enhancing effect on tPA production, amongst them several alcanoic acids including acetate at 5 mM. Only proprionate, valerate and, with outstanding effect, butyrate were found to have such effect. Acetate did not differ significantly from the control.

It is an object of the present invention to avoid the disadvantages of the prior art and to devise another method for enhancing the yield of product protein in animal cell culture. This object is achieved according to the present invention by a method for culturing animal cells wherein a cell culture medium is supplemented with acetate; another object of the present invention are the corresponding cell culture media comprising acetate according to the present invention.

Possible embodiments of the invention are shown in the figures and tables:

BRIEF DESCRIPTION OF THE DRAWINGS

FIG. 1 shows the effect of potassium and sodium acetate on NS0 productivity in fed-batch shake flask culture.

FIG. 4 compares the effect on NS0 of inclusion of sodium acetate in inoculum cultures (in inoc) and the timing of further acetate addition (at inocculation or during mid-exponential phase, i.e. at feed). All values are expressed as percent difference compared to control.

Figure 2:
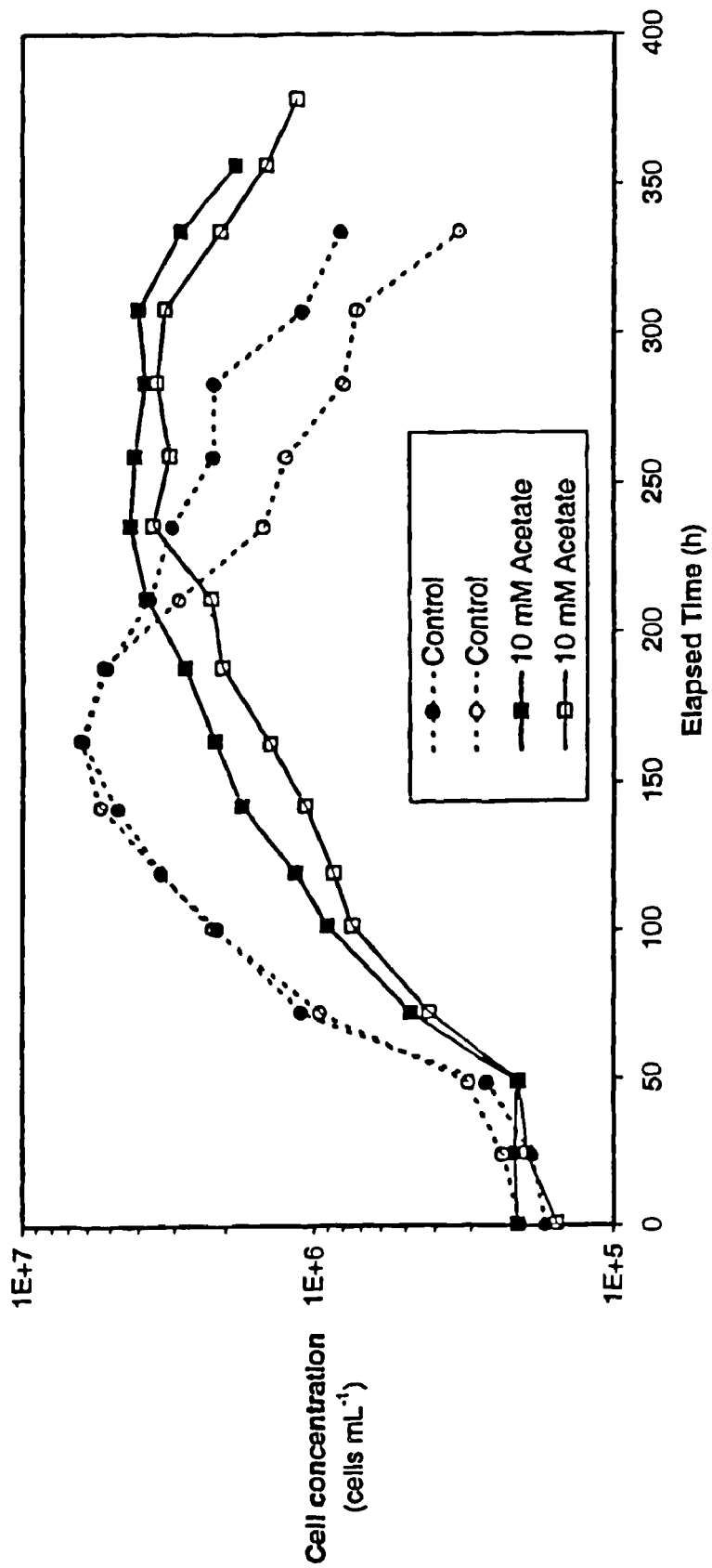
FIG. 2 shows NS0 growth profiles for fed-batch bioreactor fermentations containing no or 10 mM sodium acetate.

According to the present invention, a method of producing a product protein is devised wherein the product protein is expressed from a mammalian cell in cell culture and is produced at least during a certain span of time during cell culture. That is, the product protein might either be constitutively expressed by the cell or expression might be induced at some point of time by providing a certain stimulus to the cell. Preferably, it is constitutively expressed. The method according to the present invention further comprises the steps of a) preparing a cell culture medium for mammalian cells,
b) and further adding acetic acid or an acetate salt or a biologically activated acetyl ester to a final concentration of from 1 to 20 mM, preferably of from 3 to 15 mM, more preferably of from 5 to 12 mM, most preferably of from 6 to 9.5 mM, said addition being carried out either directly to the medium prior to starting cell culture or feeding it to the medium during cell culture,
c) further culturing the mammalian cell in said medium with concomitant expression of product protein,
d) and finally harvesting said protein from the cell culture.

In a further preferred embodiment, the concentration of the acetic acid or the salt or the biologically activated ester is from 6 to 20 mM, more preferably of from 6 to 12 mM, most preferably of from 6 to 9.5 mM as may be inferred from combining the above said preferred concentration ranges.

A product gene according to the present invention is the product protein that is sought to be expressed and harvested in high amount. It may be any protein of interest, e.g. therapeutic proteins such as interleukins or enzymes or multimeric proteins or subunits of multimeric proteins such as antibodies or fragments thereof. The recombinant product gene may include a signal sequence coding sequence portion allowing secretion of the once expressed polypeptide from the host producer cell. The product protein may be a recombinant protein expressed from a transgenic promoter or it is a naturally active gene locus, such as e.g. an immunoglobuline gene locus in hybridoma cells created by conventional cell fusion techniques. Harvesting and downstream processing techniques for purification of the protein from the culture broth are well-known in the art and a routine task. Initially, techniques such as centrifugation, ultrafiltration and/or ion exchange chromatography are often applied since they allow for high-volume throughput.

An acetate salt according to the present invention can be any salt such as alkali metal or alkaline earth metal or any other metal acetate salt may be employed. Since media are usually buffered, addition of acetic acid or acetic anhydride is also conceivable, though a salt will be preferred. Likewise, easily dissociable complex salts of actetate or esters of acetic acid that are liberating acetate in situ in the culture medium during culture, either due to a high rate of hydrolysis or due to activity of cellular exoenzymes, can be employed. Such can be termed, in particular if applying to exoenzyme activity, 'biologically activatable' esters. Alkali and alkaline earth metal salts of acetate are preferred embodiments of the present invention. More preferably, the salt is an alkali metal salt with the proviso that the alkali metal is not lithium, most preferably, it is sodium acetate. Sodium acetate is particularly preferred in combination with a concentration range of 6 to 9.5 mM in a cell growth medium, as being opposed to a maintenance medium, and upon treatment of the cells with sodium acetate at the onset or prior to the onset of cell culture or both, as set forth below.

Preferably, the cell culture medium of the present invention is devoid of butyrate. Butyrate easily decreases growth rate and induces apoptosis; its concentration needs to be carefully balanced. However, according to the present invention, it can be easily substituted by acetate showing almost no or a very moderate effect on growth rate. Acetate is not known to induce apoptosis.

According to the present invention, acetate or its equivalents are added either directly to the fresh medium prior to starting cell culture or feeding it to the medium during cell culture, preferably during exponential phase growth in a growth medium. In case of feed addition, it should be taken into account that the effect of acetate takes place with some delay, i.e. a lag phase is observable with regard to the product protein yield enhancing effect. In general, addition of acetate via feed only is less effective. Addition of acetate directly to the cell culture medium, preferably a cell growth culture medium, prior to cell culturing and in the amounts stated above is strongly preferred according to the present invention, optionally in conjunction with further feed of acetate depending on the concentration. Most preferably, acetate is added only directly to the culture medium prior to culture onset, in the amounts stated above and in particular at 6 to 9 mM and in the form of sodium acetate, and is not replenished during cell cultivation via feed, preferably it is not replenished during culture growth in a suitable medium such as a high cell density growth medium.

'Addition to the medium prior to starting cell culture' according to the present invention means exposing cells at about the time of inocculation which includes the initial lag-phase before the onset of detectable growth or exposing them even prior to inocculation of the culture medium to acetate or its equivalents in the above stated amounts. Again, 'prior to inocculation' means that the inocculum pre-culture itself is grown in a medium comprising the acetate medium supplement in the above stated amounts. It is also possible to combine both aspects. In one particularly preferred embodiment, only the inocculum culture is treated with acetate in the amounts stated above whereas the cell culture growth medium used for large-scale production culture is devoid of acetate salts in the >1 mM range.

Suitable cells or cell lines can be any mammalian cell line. Suitable cell lines can be e.g. SV-40 immortalized monkey kidney cells (COS-7) cells, canine kidney cells (MDCK), african green monkey kidney cells (VERO-76), baby hamster kidney (BHK) cells such as ATCC CCL10, human liver cells (Hep G2), lymphocytic cells (Jurkat T-cell line), hybridoma cells (e.g. SP2/0-Ag14, Shulman et al. 1977) or 'myeloma' cells (such as e.g. NSO cells). It is to be understood that not all those cells will equally well respond to the addition of acetate to the cell culture medium. In addition, for a given cell type or cell line, the effect of acetate may not be linear or constant within the acetate concentration ranges specified above. Depending on cell line, it may display an individual concentration optimum at which the yield enhancing effect of acetate is maximal and is decreased when shifting acetate concentration to either lower or higher amounts; the optimum concentration may vary considerably in between cell types and may need to be established by simple dose response experimentation.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p.173 ff, 1963), Dulbecco's modified Eagle's medium (DMEM), Eagle's minimal essential medium (MEM), Ham's F12 medium (Ham, R. et al., Proc. Natl. Acad. Sc.53, p288 ff. 1965) or Iscoves' modified DMEM lacking albumin, transferrin and lecithin (Iscoves et al., J. Exp. med. 1, p. 923 ff., 1978). It is known that such culture media can be supplemented with fetal bovine serume (FBS, also called FCS), the latter providing a natural source of a plethora of hormones and growth factors. Cell culture of vertebrate and mammalian cells, respectively, has become a routine matter and is covered in detail e.g. in R. Ian Fresney, Culture of Animal cells, a manual, 4$^{th}$ edition, Wiley-Liss/N.Y., 2000.

Preferably, the cell culture medium according to the present invention is a medium allowing for and supporting growth of the animal cells thus cultured. Growth is understood as an increase in viable cell density during at least a certain period of the cell culture. According to the present invention, such definition of 'growth medium' is to be understood as being opposed to the term 'maintenance medium' in its usual meaning in the art. A maintenance medium is a cell culture medium which supports cell viability but which does not encourage cell growth. Often, such maintenance media do not contain essential growth factors such as transferrin, insulin, albumin and the like.

Said embodiment of the medium being a mammalian cell culture medium comprising acetate or its equivalents in the afore mentioned amounts applies in particular to culturing or to a medium suited for the culture of lymphoid cells such as e.g. hybridoma and myeloma cells. The term hybridoma includes not only antibody secreting cells obtained by cell fusion, including so-called quadromas and the like, but as well B-lymphocytic, antibody secreting cells obtained by immortalization with an immortalizing agent such as a recombinant gene product having cell cycle activity or a virus, e.g. Eppstein-Barr-Virus, or any chemical, immortalizing agent. In the present context, 'hybridoma' extends as well to non-secreting hybridomas such as e.g. SP2/0-Ag14, Shulman et al. 1977. Therefore, a product protein sought to be harvested from a hybridoma in the present context does not relate necessarily to a homologous gene product such as an antibody from a parent cell but may as well be a recombinant product protein.

Preferably the cells are 'myeloid', most preferably they are a myeloma NS0 cell line (such as e.g. cell line ECACC No. 85110503 and derivatives thereof, freely available from the European Collection of Cell Cultures (ECACC), Centre for Applied Microbiology & Research, Salisbury, Wiltshire SP4 0JG, United Kingdom). 'Myeloid' cells are tumor cell lines of which NS0 is one example. NS0 cells are actually plasmacytomas and are in consequence of B-lymphocytic lymphoid cell lineage as are hybridomas, though being addressed in the art routinely and quite incorrectly as being 'myeloid' cells (Barnes et al., Cytotechnology 32:109-123, 2000). Corresponding cell types are likewise particularly preferred embodiments in consequence. 'Myeloma' NS0 cells have been found to give potentially rise to extremely high product yields, in particular if used for production of recombinant antibodies. Most standard NS0 cell lines are cholesterol-dependent, usually making cholesterol an obligate component of the culture medium. According to the present invention, lymphoid cells do comprise hybridoma cells generated by a number of techniques from antibody-secreting cells such as cell fusion with suitable tumor cell lines, including fusion with non-secreting hybridoma cell lines which gives rise to so-called triomas, or immortalisation with a transforming agent or virus as well as any other lymphoid cell line. In another preferred embodiment, however, a mammalian cell or cell line according to the present invention, is not a hybridoma cell line, meaning it is a non-hybridoma cell line, and more preferably it is a non-hybridoma, recombinant cell line, most preferably a recombinant 'myeloma' cell line as defined above.

In a further preferred embodiment, the cell line is a NS0 cell line which is capable to express recombinant glutamine synthetase (GS). NS0 cells are specifically of advantage if used with the Glutamine synthetase (GS) expression system (Bebbington et al., 1992, High-level expression of a recombinant antibody from myeloma cells using a glutamine synthetase gene as an amplifiable selectable marker, Bio/Technology 10:169-175; Cockett et al., 1990, High level expression of tissue inhibitor of metalloproteinases in Chinese Hamster Ovary (CHO) cells using Glutamine synthetase gene amplification, Bio/Technology 8: 662-667). Preferably, the product protein gene sequence and the GS gene sequence are carried on a single GS plasmid vector for generating said transfected NS0 cell line, said genes either being expressed from different or same promoters employing e.g. internal ribosome entry sites.—The GS-system is one of only two systems that are of particular importance for the production of therapeutic proteins. In comparison to the dihydrofolate reductase (DHFR) system, the GS system, and in particular the GS system used in combination with NS0 myeloma cells, offers a large time advantage during development because highly productive cell lines can often be created from the initial transfection thus avoiding the need for multiple rounds of selection in the presence of increasing concentrations of selective agent in order to achieve gene amplification (Brown et al., 1992, Process development for the production of recombinant antibodies using the glutamine synthetase (GS) system, Cytotechnology 9:231-236). NS0 cells are phenotypically deficient in Glutamine-synthetase. Therefore the NS0 cell line which was derived from a mouse tumour cell line (Galfre, G. and Milstein, C., Methods in Enzymol. 73, 3-75, 1981) is frequently the cell line of choice used in combination with the GS system at an industrial scale.

Preferably, the cell culture medium according to the present invention is devoid of fetal calf serum (FCS or FBS), which then is being termed 'serum-free'. Cells in serum-free medium generally require insulin and transferrin in a serum-free medium for optimal growth. Transferrin may at least partially be substituted by non-peptide chelating agents or siderophores such as tropolone as described in WO 94/02592 or increased levels of a source of anorganic iron favorably in conjunction with antioxidants such as vitamin C. Most cell lines require one or more of synthetic growth factors (comprising recombinant polypeptides), including e.g. epidermal growth factor (EGF), fibroblast growth factor (FGF), insulin like growth factors I and II (IGFI, IGFII), etc. Other classes of factors which may be necessary include: prostaglandins, transport and binding proteins (e.g. ceruloplasmin, high and low density lipoproteins, bovine serum albumin (BSA)), hormones, including steroid-hormones, and fatty acids. Polypeptide factor testing is best done in a stepwise fashion testing new polypeptide factors in the presence of those found to be growth stimulatory. Those growth factors are synthetic or recombinant. There are several methodological approaches well-known in animal cell culture, an exemplary one being described in the following. The initial step is to obtain conditions where the cells will survive and/or will grow slowly for 3-6 days after transfer from serum-supplemented culture medium. In most cell types, this is at least in part a function of inoculum density. Once the optimal hormone/growth factor/polypeptide supplement is found, the inoculum density required for survival will decrease.

In a more preferred embodiment, the cell culture medium according to the present invention is protein-free, more preferably it is a protein-free growth medium, that is it is free both of fetal serum and individual protein growth factors supplements or other protein such as recombinant transferrin or serum albumin for lipid binding and transport. Most preferably, it is a protein free medium as defined above but to which has been added recombinant or purified albumin or a sequence variant or fragment thereof. It should be noted, however, that even for NS0 cell lines which usually require cholesterol as a medium supplement, obtention of cholesterol-independent subspecies has been reported which can be continuously cultured and grown for protein production (Lonza Biologics, UK). Protein-free culture media according to the present invention are particularly preferred in conjunction with the use of myeloma cell lines such as NS0.

A further preferred, possible embodiment of the method and the below specified cell culture medium of the present invention is high-density fermentation or high-density growth fermentation of the animal cells, e.g. in an industrial fed-batch bioreactor such as an airlift or perfusion bioreactor up to or beyond a viable cell density of up to or beyond $10^5$ cells/ml, preferably $10^6$ cells/ml. Consequently, a high-density growth culture medium has to be employed. Such high-density growth media can usually be supplemented with nutrients such as all amino acids, energy sources such as glucose in the range given above, inorganic salts, vitamins, trace elements (defined as inorganic compounds usually present at final concentrations in the micromolar range), buffers, the four nucleosides or their corresponding nucleotides, antioxidants such as Glutathione (reduced), Vitamin C and other components such as important membrane lipids, e.g. cholesterol or phosphatidylcholine or lipid precursors, e.g. choline or inositol. A high-density medium will be enriched in most or all of these compounds, and will, except for the inorganic salts based on which the osmolarity of the essentially isotonic medium is regulated, comprise them in higher amounts (fortified) than the afore mentioned standard media as can be incurred from EP-435 911 A or GB-2251249 in comparison with RPMI 1640. GB-2251249 gives examples of suitable high-density growth media. In accordance with the present invention, such high density cell culture medium comprises acetate in the amounts stated above, preferably in the absence of a butyrate. Further preferred, a high-density culture medium according to the present invention is balancedly fortified in that a majority of amino acids except for Tryptophane are in excess of 75 mg/l in the culture medium. More preferably, in conjunction with the general amino acid requirement, the joint amounts of Glutamine and Asparagine are in total in excess of 1 g/l, most preferably in excess of 2 g/l of high-density culture medium. It goes without saying that the latter more preferred embodiment is less suitable in case of a recombinant cell line transfected with a Glutamine synthetase (GS) vector, in particular after rounds of amplification of the GS gene sequence have taken place. In those cells, an excess of e.g. glutamine jointly from exogenous and endogenous source would lead to production of ammonia, which is to be avoided.

In the context of the present invention, high-density cell culture is defined as a population of animal cells having temporarily a density of viable cells of at least or in excess of $10^5$ cells/ml, preferably of at least or in excess of $10^6$ cells/ml, and which population has been continuously grown from a single cell or inoculum of lower viable cell density in a cell culture medium in a constant or increasing culture volume.

In a further preferred embodiment, the cell culture according to the present invention is a fed-batch culture wherein one or several other amino acids, preferably comprising at least Glutamin, is fed to the cell culture as described in GB-2251249 for maintaining their concentration in the medium and apart from controlling Glucose concentration by separate feed. More preferably, the feed of Glutamin and optionally one or several other amino acids, ideally comprising Glutamine is combined with feeding one or more energy sources such as glucose to the cell culture as described in EP-229 809-A. Glutamine may at least be partly substituted by Asparagine (for substitution of glutamine by asparagine, see Kurano, N. et al., 1990, J. Biotechnology 15, 113-128). Feed is usually initiated at 25-60 hours after start of the culture; for instance, it is useful to start feed when cells have reached a density of about $10^6$ cells/ml. The amino acids that can be present in the feed are usually dosed in the range of from 10 to 300 mg total addition per amino acid per liter of culture volume; in particular glycine, lysine, arginine, valine, isoleucine and leucine are usually fed at higher amounts of at least 150 to 200 mg per L of culture volume as compared to the other amino acids. Except for GS cell lines, it can be of benefit to adjust the total feed of glutamine and/or asparagine to the range of from 0.5 to 3 g per L of culture volume, preferably to the range of from 1 to 2 g per L of culture volume. The feed can be added as shot-addition or as continuously pumped feed, preferably the feed is almost continuously pumped into the bioreactor. It goes without saying that the pH is carefully controlled during fed-batch cultivation in a bioreactor at an approximately physiological pH optimal for a given cell line by addition of base or buffer. When glucose is used as an energy source the feed of glucose feed is adjusted usually to keep glucose concentration of the medium of from 1 to 10 grams, preferably of from 3 to 6 grams per liter of the culture. Apart from inclusion of amino acids, the feed preferably comprises a low amount of choline in the range of 5 to 20 mg per liter of culture.

A corresponding cell culture medium comprising an acetate supplement suited e.g. for NS0 cell culture, a cell culture made up of such cell culture medium and lymphoid and/or NS0 cells and a medium concentrate for preparing such medium are further objects of the present invention. The above description applies likewise to these embodiments of the present invention.

EXPERIMENTS

Where not specified, antibody productivity or titer was determined by protein A-HPLC.

Experiment 1

The GS-NS0 cell line 6A1(100)3, 6A1 for short, secreting recombinant mouse/human chimeric IgG cB72.3 (Bebbington, 1992, supra) was used in all experimental settings under this section. Cell culture was either carried out in shake flask culture or in a fed-batch mode in a 10l standard airlift bioreactor, essentially as described (Bebbington, 1992). Feeds essentially comprised amino acids and carbohydrate as described above for high-density media and fermentation, respectively. Feed volume was at 4% of post-inoculation volume. Feed was initiated at a rate of 0.2 ml/Lh when viable cell density exceeded $14 \times 10^5$ cells/ml. Temperature was controlled at 36.5 degree centigrade; for airlift, air saturation was at 15%. pH was controlled at pH 7.00. Culture was inoculated at $2 \times 10^5$ viable cells/ml. Medium is serum- and essentially protein-free growth medium ProCH04-CDM (BioWhittaker) supplemented with 50 mM methionine sulfoximine (MSX). Cells were pre-adapted to medium. Increases in protein yield of up to 98% (from 470 mg/L of the control as compared to 768 mg/L for a strain grown with 10 mM acetate) were observed. Acetate was found not to suppress growth. It slightly decreased growth rate but did not lower maximum viable cell densities. Positively, it did prolong stationary phase upon fermentation.

Cumulative cell time ($10^6$ cell/h ml) was calculated by integration of the cell growth curve, essentially as described by Renard et al. (1988, Biotechnology Letters 10, 91-96).

FIG. 1 shows the effect of potassium and sodium acetate on productivity in fed-batch shake flask culture. Either sodium acetate or potassium acetate were added to shake flask culture during mid-exponential growth phase to the final concentrations stated in the respective sections of the table of FIG. 1. Cultures were counted daily by Trypan blue method and samples were taken for product analysis by means of protein A fractionation and HPLC analysis. Sodium acetate at 10 mM performed even better than potassium acetate at either 10 mM or 15 mM. The CCT was similar in all treatments (including control). Consequently, single cell productivity ($q_p$) was found to be increased.

Figure 3:
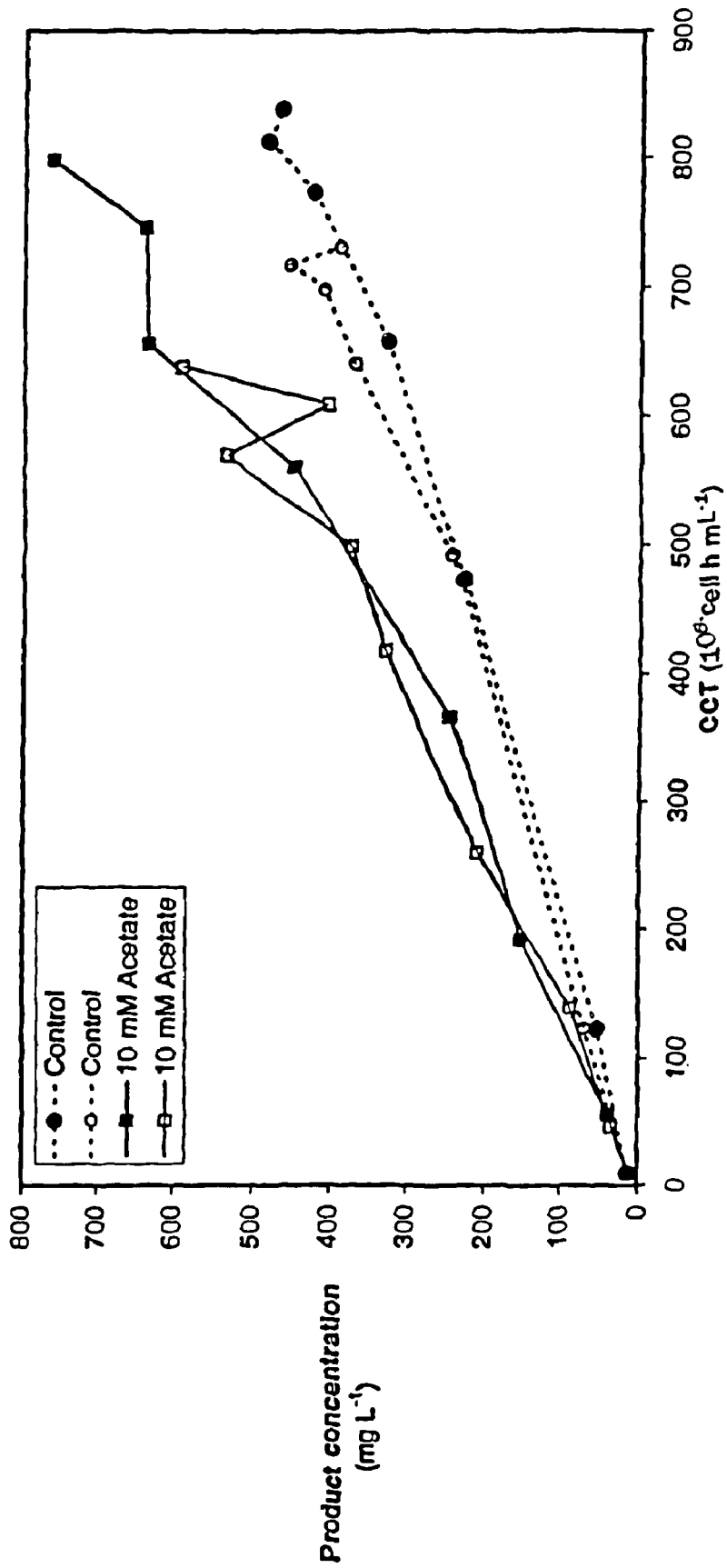
FIG. 3 shows the effect of 10 mM sodium acetate on NS0 productivity in the fermentation run according to FIG. 2.

FIG. 2 shows growth profiles for fed-batch bioreactor fermentations containing no or 10 mM sodium actetate. Duplicate cultures both for control and 10 mM sodium acetate supplemented culture were tested for viable cell concentration (determined by Trypan blue exclusion standard counting test). Feed was started at day 4. The acetate was not fed during growth phase as in FIG. 1 but was included in cell culture production medium right away to which the inoculum cells were added. As can be seen, the yield enhancing effect of acetate proved to be highly reproducible (FIG. 3) as was growth behavior. No significant growth suppression could be observed in terms of maximum cell density achievable. Growth rate was not substantially decreased though a certain effect of acetate addition was reproducibly found. The CCT remained essentially similar for all cultures. Notably, acetate improved duration or stability of stationary growth phase; decline of viable cell density after viable cell density peaked was much slower in the presence of acetate. Antibody production is known to be much higher in stationary phase than in exponential growth phase.

In an additional set of experiments, the feed was further supplemented with LiCl both for the control and the culture treated with acetate as said in the preceding paragraph, accumulating to a final concentration of approx. 1-10 mM (data not shown). The addition of a Li-salt did not prove to modify the effect of acetate addition in any way. Certainly, no synergistic enhancement of the effect of acetate addition could be seen as has been reported for n-butyrate supplementation of cultures.

FIG. 4 compares the effect of inclusion of sodium acetate in inoculum cultures (in inoc) or at the time of inoculation to the production medium (at inoc) or in the feed given during mid-exponential phase (at feed) or combinations thereof in fed-batch shake flask culture. All values are expressed as percent difference compared to control. A clear dose dependency was observable as regards the amount of acetate added. Addition of acetate to the inoculum culture or at the time of inoculation, meaning the use of an acetate supplemented culture medium for production culture, was found to be the most effective mode in view of increased yield and maximized single cell productivity.

Experiment 2

Figure 5:
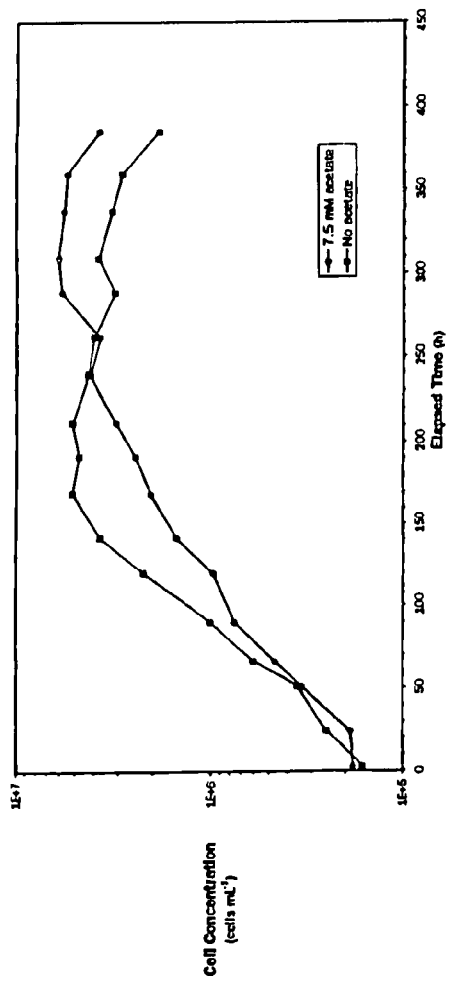
FIG. 5 shows the growth and antibody productivity of recombinant NS0 cells with 7.5 mM acetate in a custom-made high-density growth medium.
Figure 6:
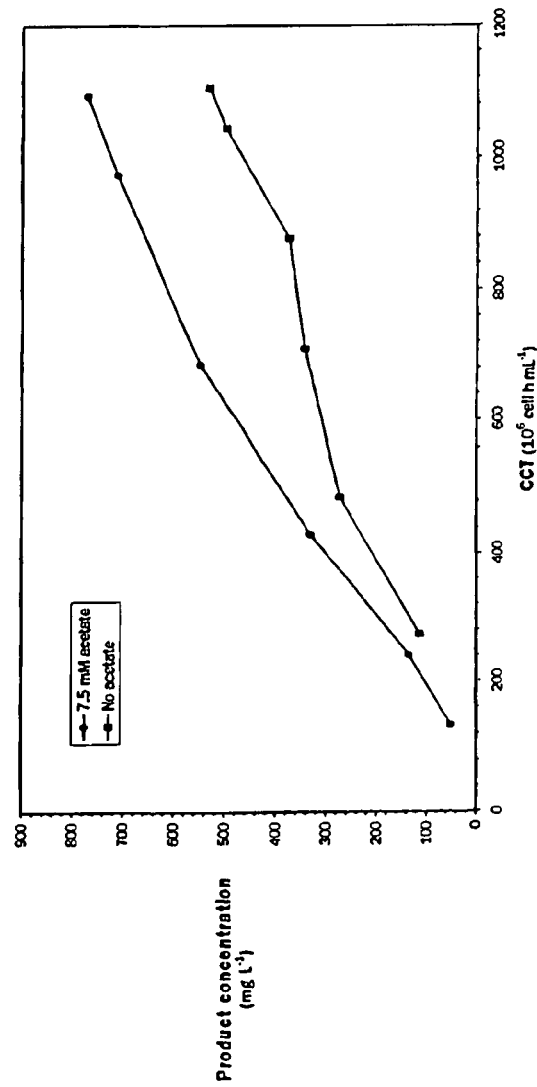
FIG. 6 shows the growth and antibody productivity of recombinant NS0 cells with 7.5 mM acetate in a custom-made high-density growth medium.

Exp. 2 was conducted essentially as described above for exp. 1/FIG. 2, except that now 7.5 mM sodium acetate and a proprietary high-density culture medium was used, similar to the lipid supplemented high-density media described in EP435 911 A but distinct in employing less ethanolamine and no thioglycerole and keeping Tryptophan concentration constant at 19 mM by sensor-controlled automatic feeding. With such medium, 7.5 mM acetate was found to be optimal for that cell line with regard to antibody yield and process robustness. FIG. 5 shows the CCT diagram for 7.5 mM acetate, demonstrating again that the application of acetate allows of enhancing antibody yield without decreasing growth rate or viable cell density. In contrast to exp. 1, the same maximum viable cell density could be achieved in the presence of actetate as compared to the control without acetate in the absence of any adverse effect on duration of stationary phase growth. Similarly, product concentration increased steadily over control and over time (FIG. 6). Unlike other productivity enhancing agents, such as sodium butyrate, addition of sodium acetate leads to only small decreases in cell growth parameters (cell growth rate and cumulative cell time). Thus addition of sodium acetate leads to a large increase in the harvest antibody concentration.

Experiment 3

Figure 7:
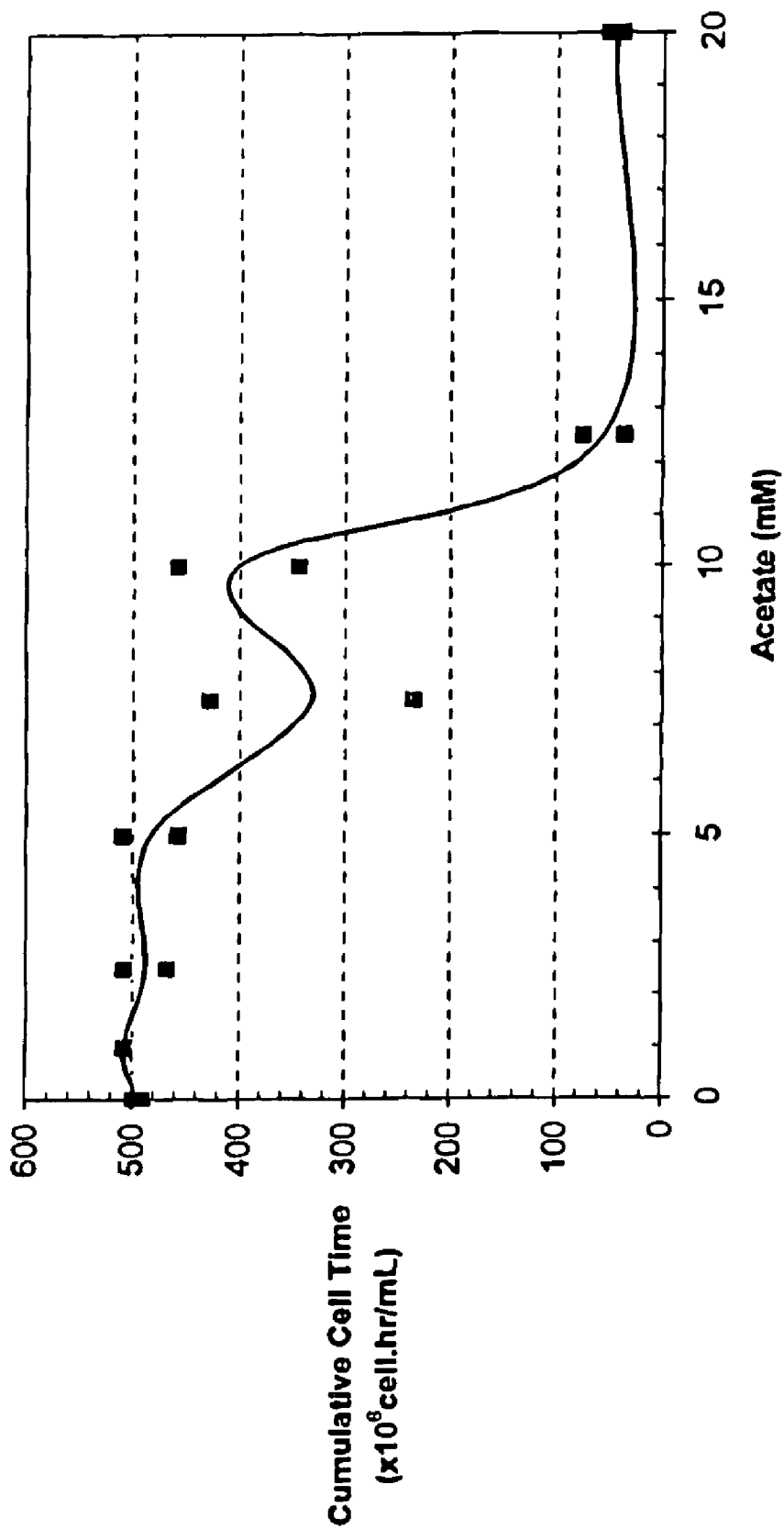
FIG. 7 shows dose-response curves for supplementation of NS0 cell culture with sodium acetate.
Figure 8:
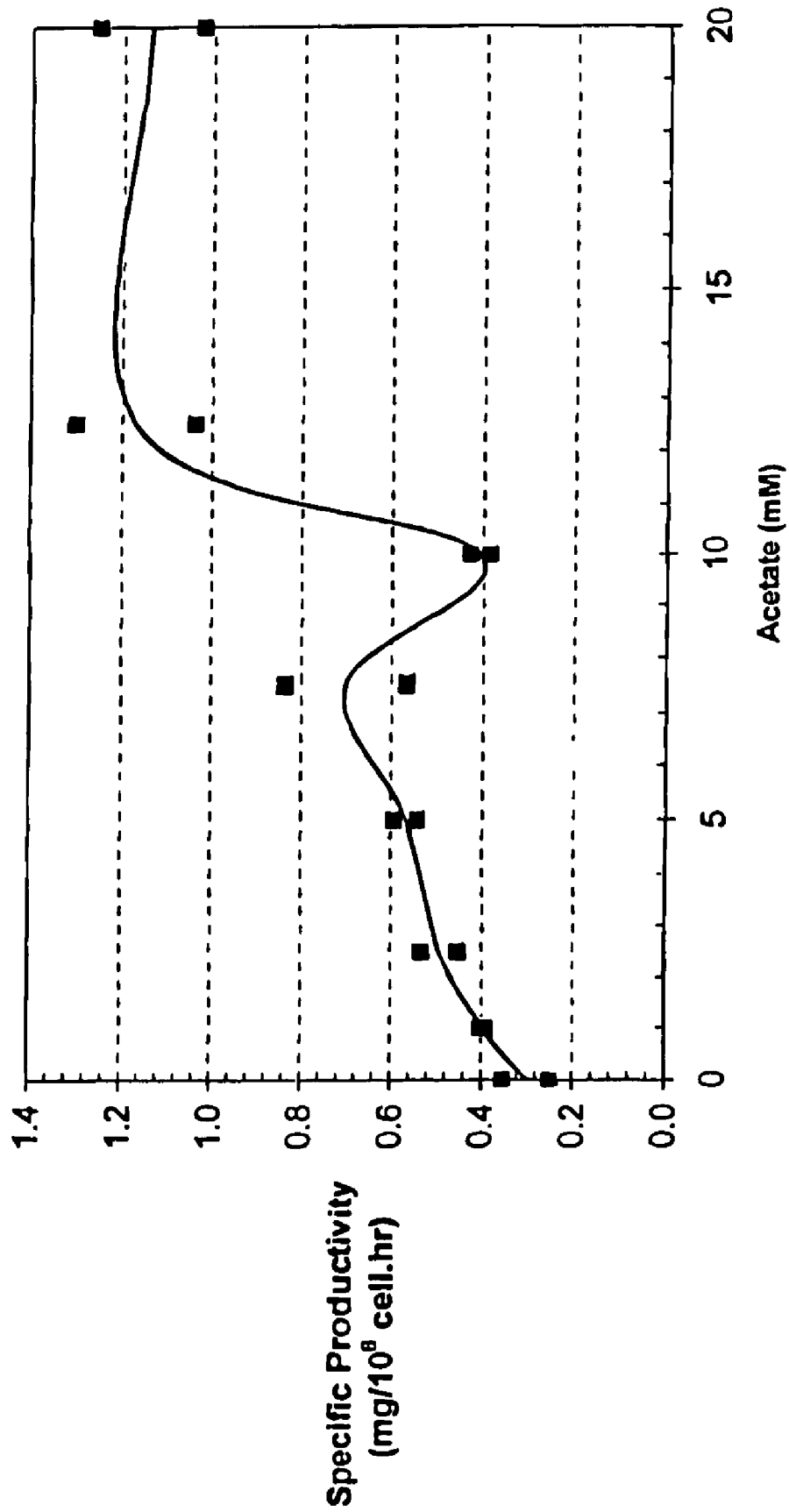
FIG. 8 shows dose-response curves for supplemental of NS0 cell culture with sodium acetate.

The experiment was a dose-response study for the addition of different amounts of sodium acetate for NS0 cell line 6A1 in the range of up to 20 mM and was conducted essentially as described in exp. 1/FIG. 2. FIG. 7 shows CCT dependent on dose of acetate added, FIG. 8 shows single cell specific productivity ($q_p$) dependent on dose of acetate added.

Comparative Example

Experiment 4

Figure 9:
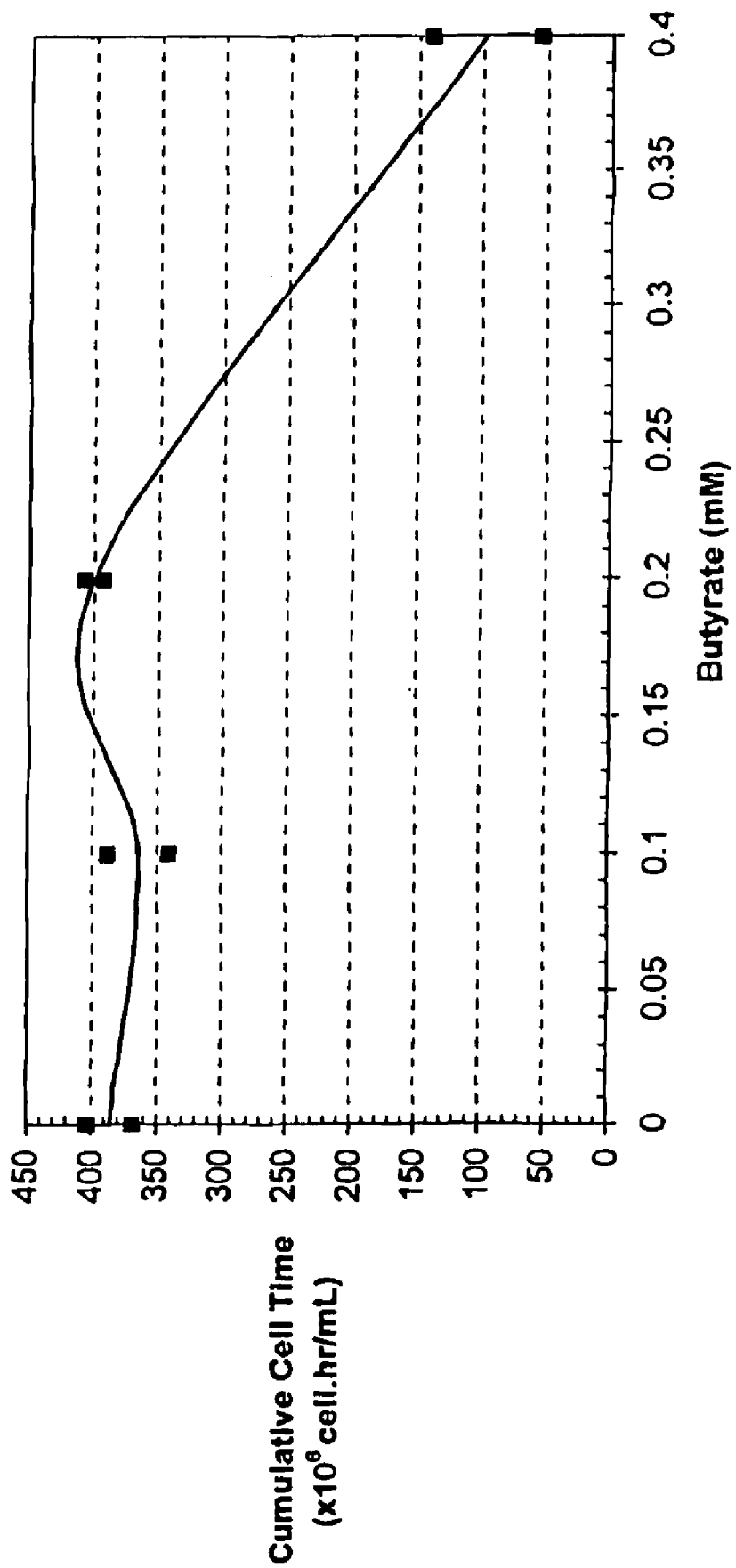
FIG. 9 shows comparative data for supplementation of NS0 cell culture medium with sodium n-butyrate.
Figure 10:
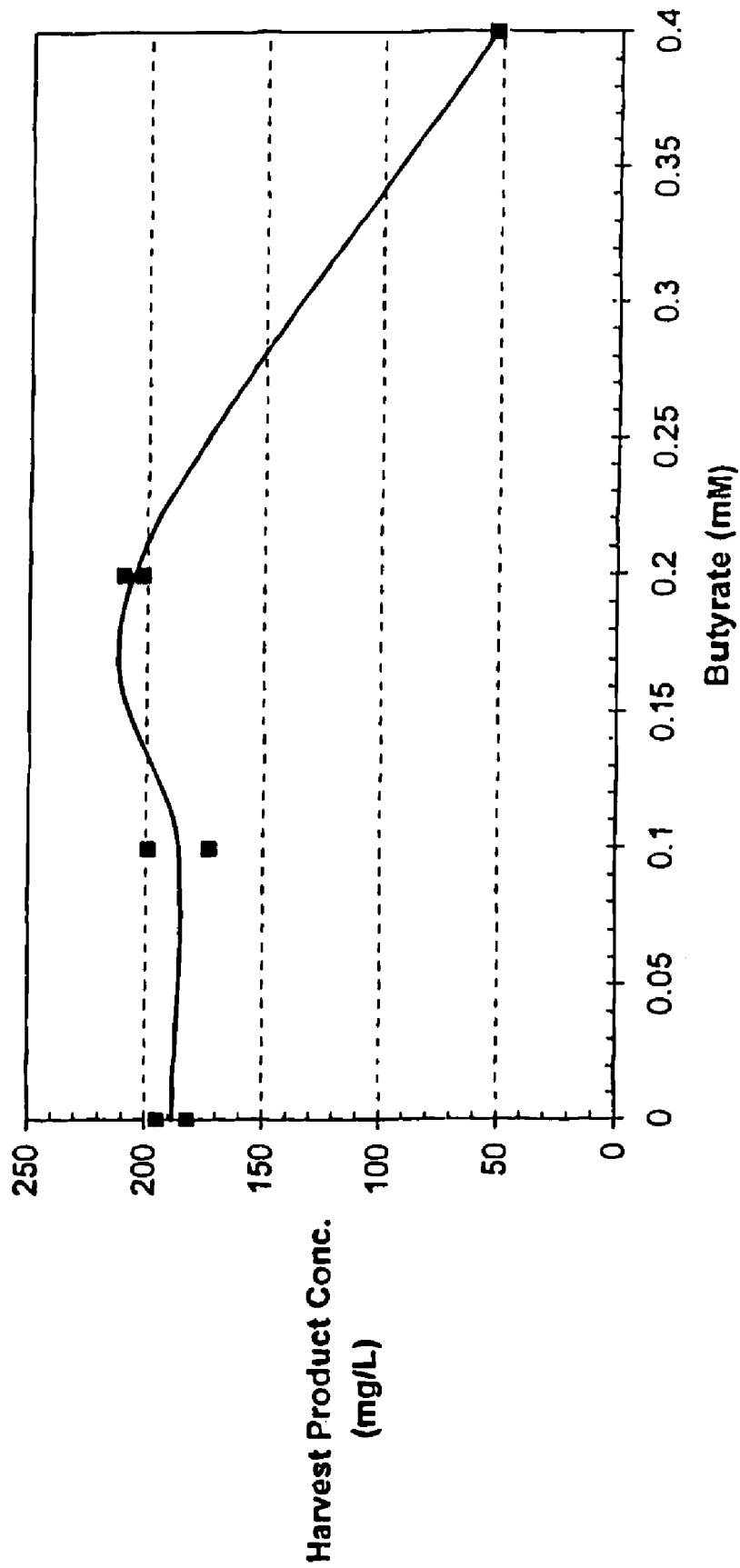
FIG. 10 shows comparative data for supplementation of NS0 cell culture medium with sodium n-butyrate.
Figure 11:
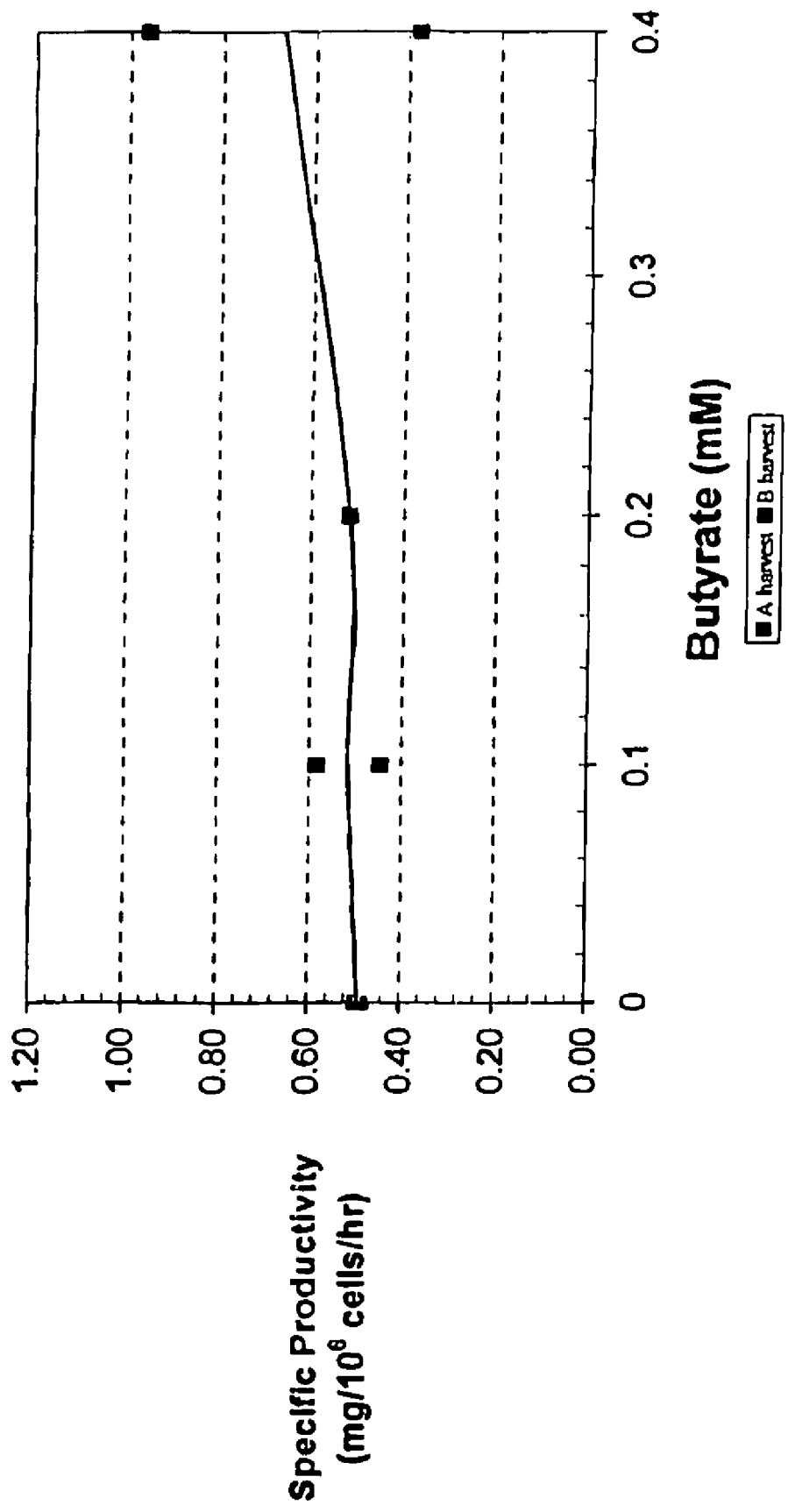
FIG. 11 shows comparative data for supplementation of NS0 cell culture medium with sodium n-butyrate.

Butyrate addition to cell culture media does not increase antibody productivity in NS0-6A1 cells; at doses >1 mM, it is strongly toxic to the cells and decreases viable cell density very rapidly. In the permissible range, no increase in productivity could be seen at all, not even at the single cell level. The experiment was conducted essentially as described in exp. 1/FIG. 2, except that butyrate was added in the amounts shown instead of acetate. Later addition of butyrate at the mid-exponential phase did not enhance productivity, either. FIG. 9-11 show the effect of butyrate addition on CCT, antibody titer at harvest and single cell specific productivity ($q_p$).

Experiment 5

Figure 12:
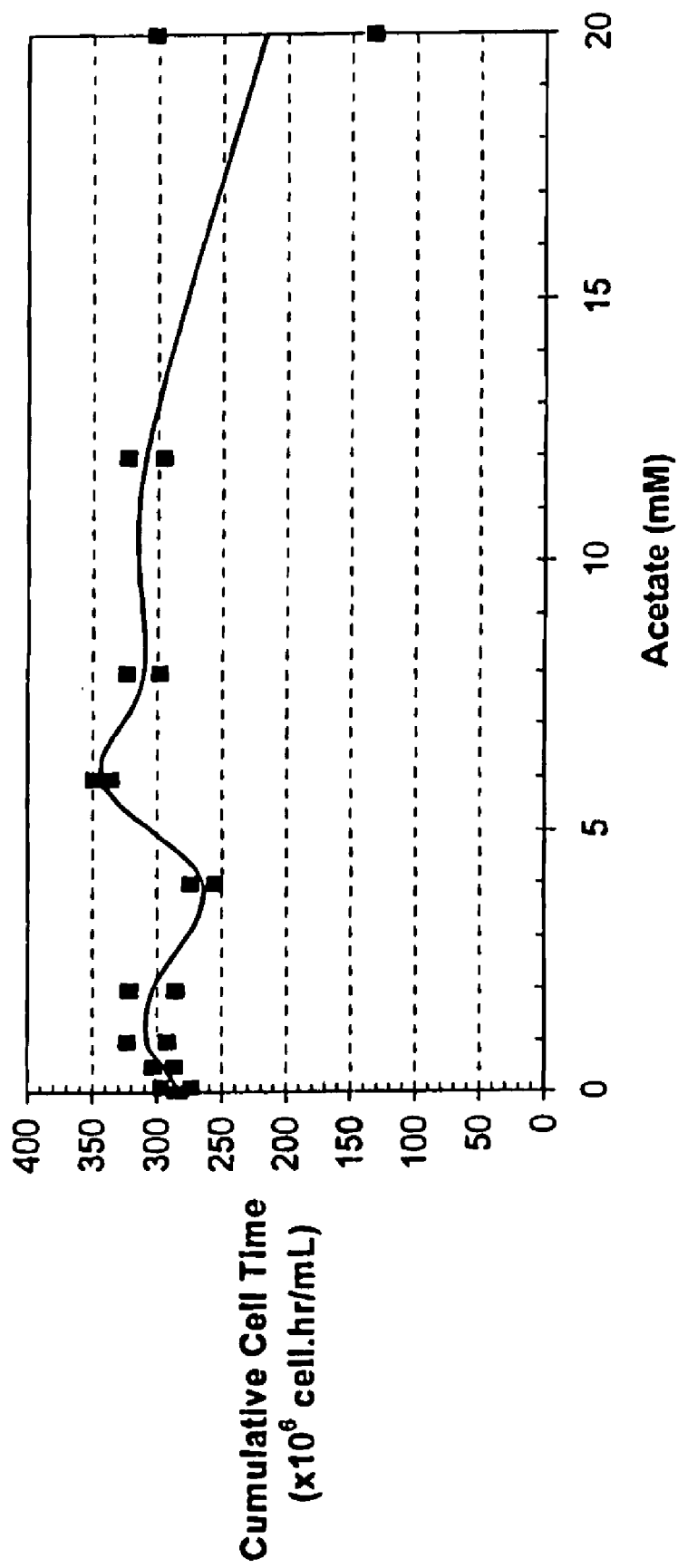
FIG. 12 shows dose-response curves for supplementation of a VPM 8 hybridoma cell culture with sodium acetate.
Figure 13:
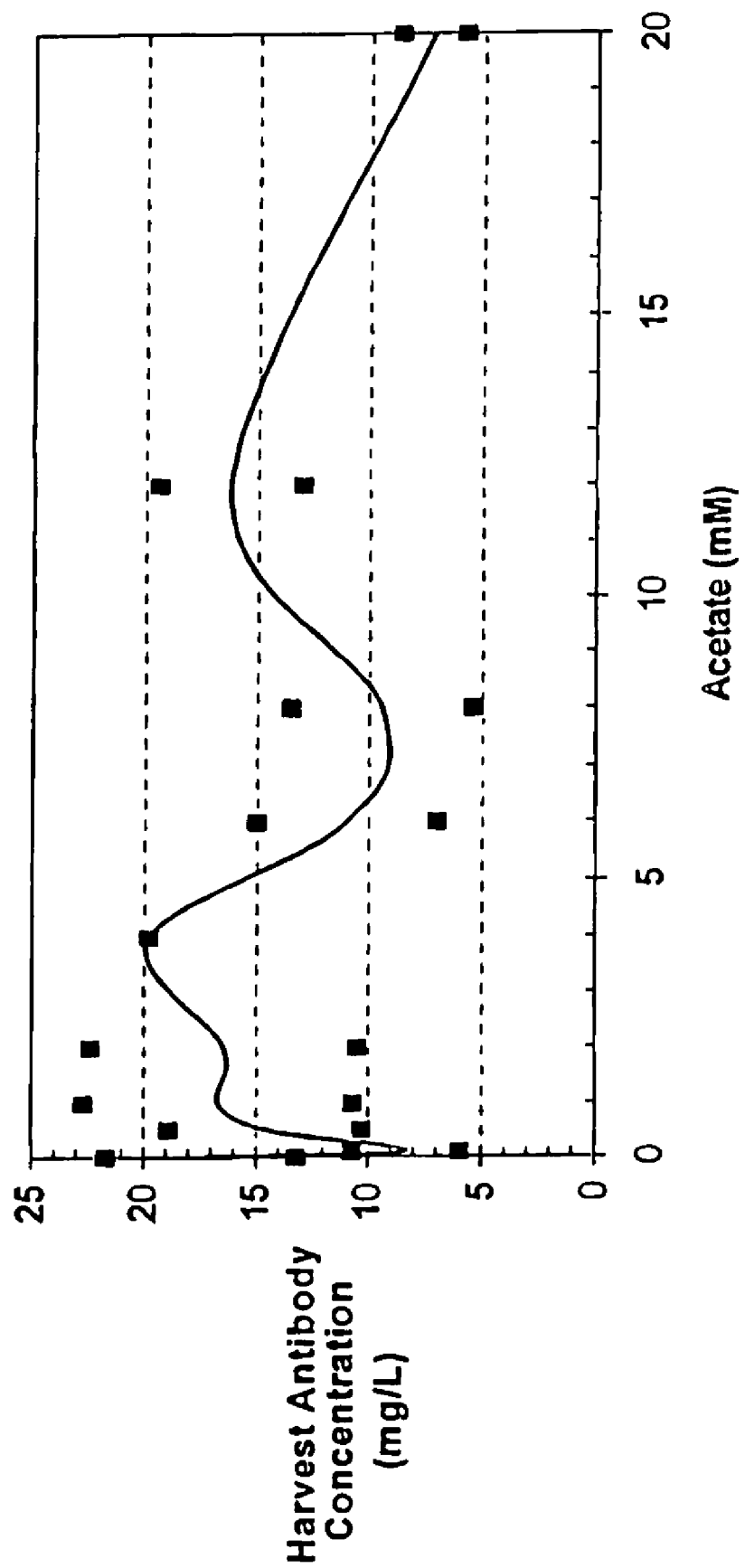
FIG. 13 shows dose-response curves for supplementation of a VPM 8 hybridoma cell culture with sodium acetate.
Figure 14:
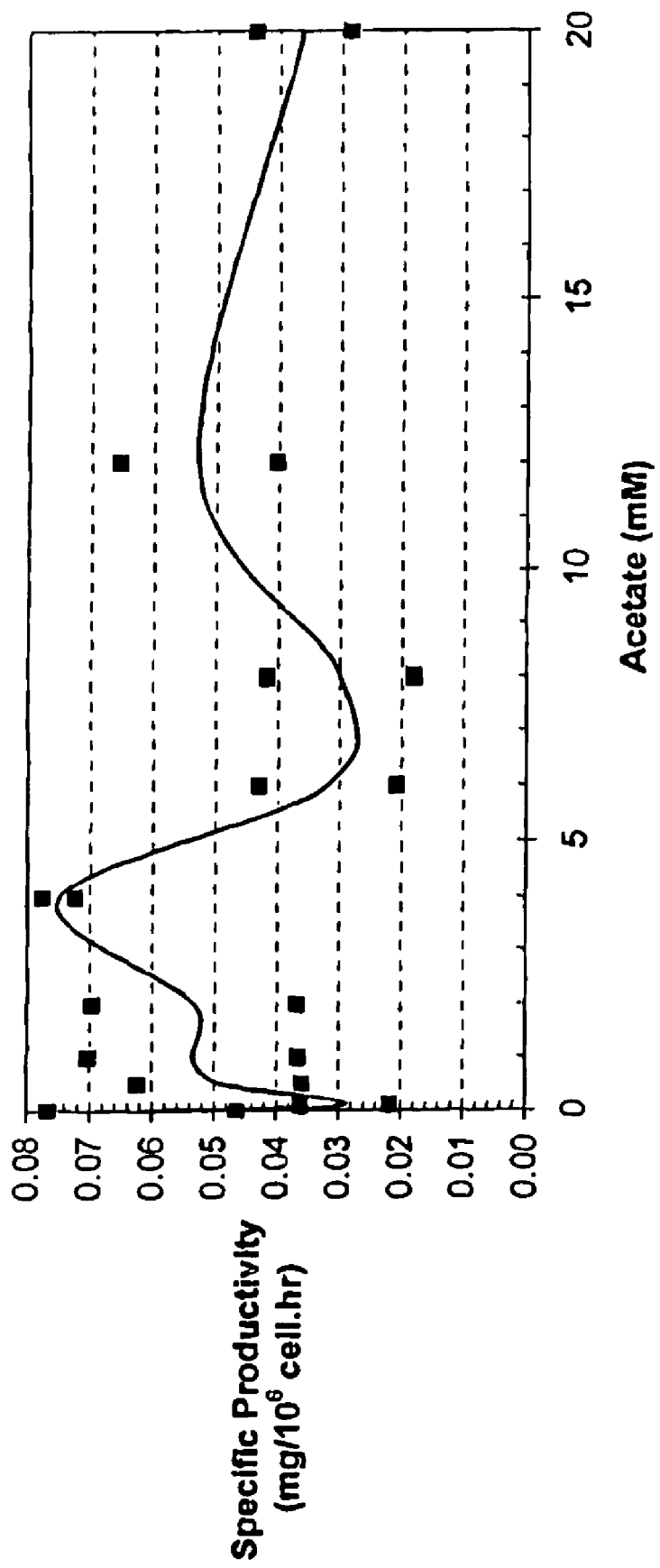
FIG. 14 shows dose-response curves for sipplementation of a VPM 8 hybridoma cell culture with sodium acetate.

A dose response study for addition of sodium acetate was carried out for hybridoma cell line VPM 8 (ECACC No. 93113024, European Collection of cell cultures, supra) essentially as described in exp. 3, except that VPM 8 was grown in commercial, protein-free medium CD-Hybridoma (Invitrogen/U.K.) and in that no MSX was added, since not being a GS cell line. VPM 8 is a mouse hybridoma that was generated by conventional means of cell fusion with non-secreting myeloma cells and secretes a murine IgG1 antibody. FIG. 12-14 show the effect of acetate addition on CCT, antibody titer at harvest and single cell specific productivity ($q_p$). Notably, in comparison to butyrate, the hybridoma VPM 8 tolerates acetate surprisingly easily in the mM range, in contrast to butyrate (s. exp. 6) and shows enhanced productivity as compared to non-acetate treated control. The latter could not have been expected based on butyrate treatment of such cells known from the prior art (s. exp. 6).

Comparative Example

Experiment 6

Figure 15:
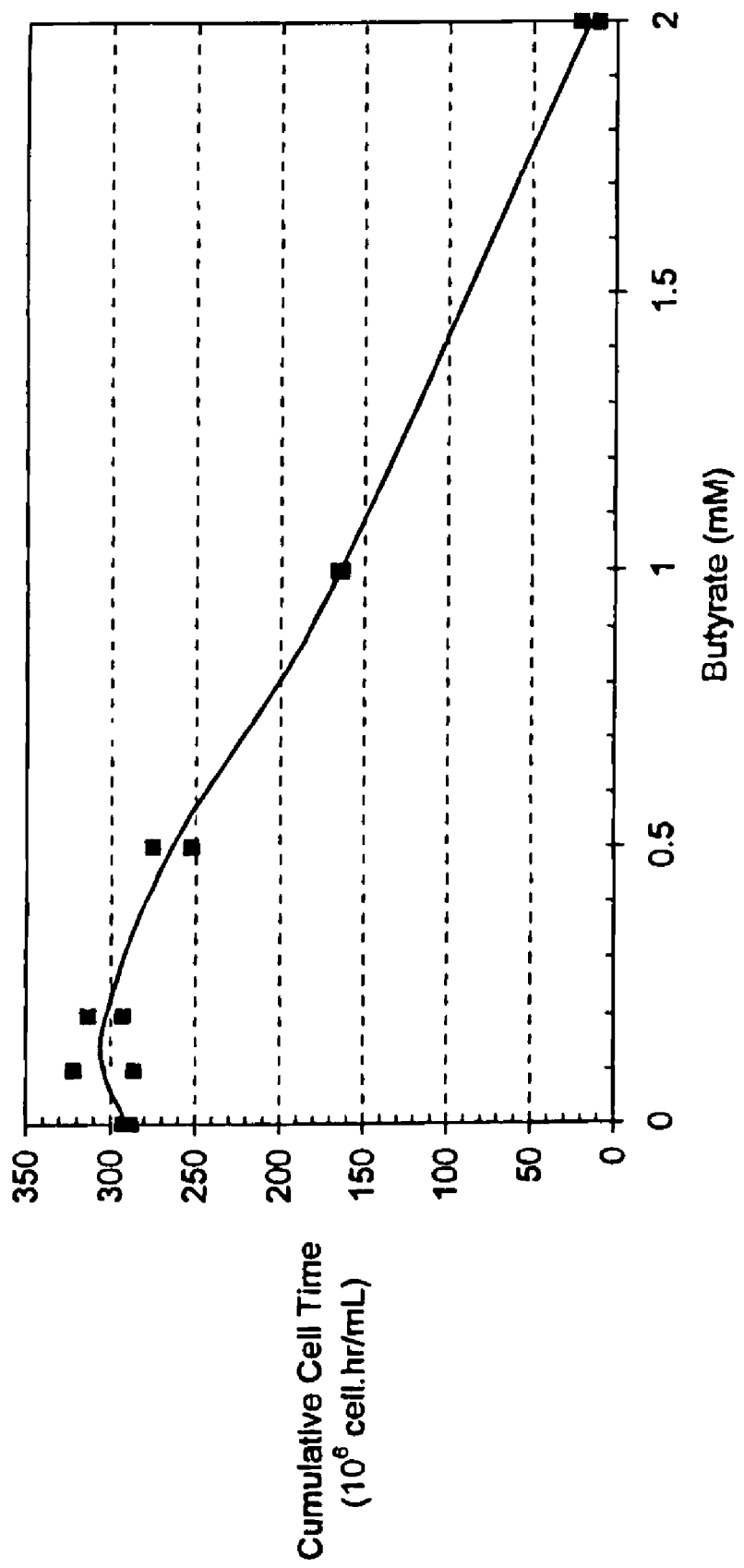
FIG. 15 shows comparative data for supplementation of a VPM 8 hybridoma cell culture with sodium n-butyrate.
Figure 16:
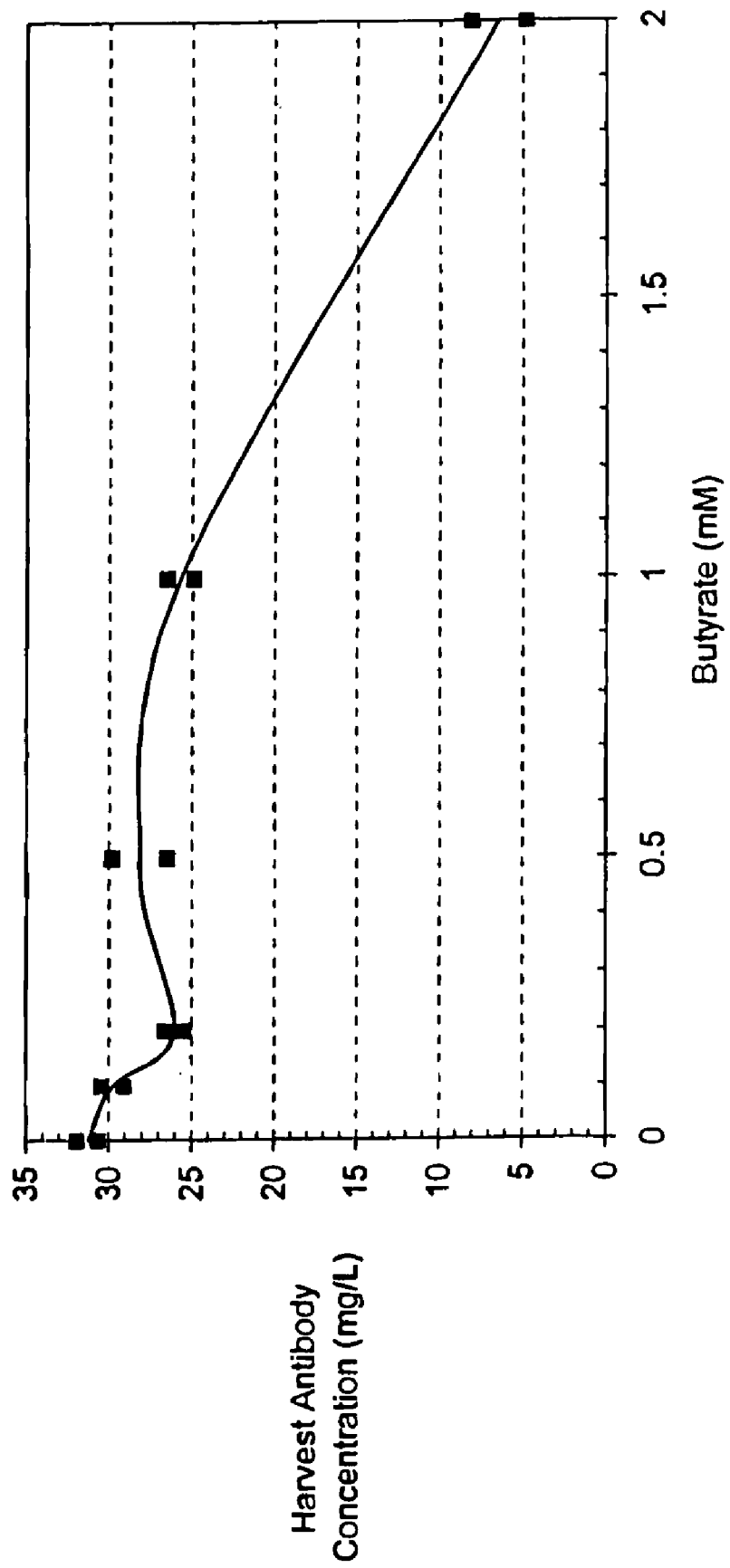
FIG. 16 shows comparative data for supplementation of a VPM 8 hybridoma cell culture with sodium n-butyrate.
Figure 17:
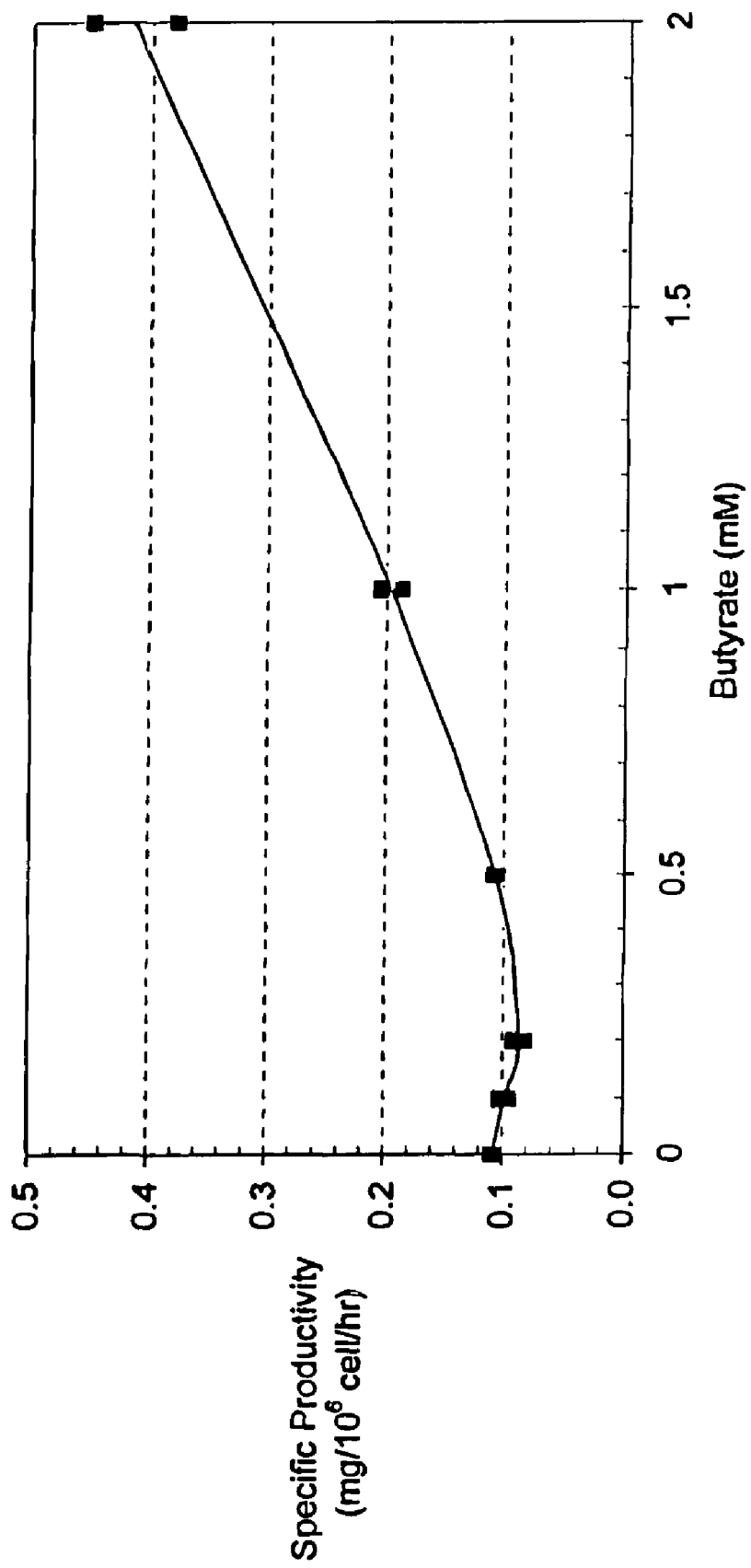
FIG. 17 shows comparative data for supplementation of a VPM 8 hybridoma cell culture with sodium n-butyrate.

FIG. 15-17 show the effect of n-butyrate treatment of VPM 8 hybridoma cells on CCT, harvest antibody titer and single cell specific productivity ($q_p$), respectively. The experiment has been carried out essentially as described in exp. 5, except that acetate was substituted with n-butyrate in the amounts stated in the figures. Given the exceptional toxicity of butyrate for this cell line, it is hardly possible to add any butyrate at all without decreasing growth rate and viable cell density. Butyrate supplementation therefore is not effective in increasing antibody titer.

The invention claimed is:

1. A lymphoid cell culture media, characterised in that the medium is serum free and comprises an alkali metal salt of acetate or an alkaline earth metal salt of acetate or a metal acetate salt at a concentration of from 5 to 20 mM, said cell culture medium being free of butyrate and said alkali metal not being lithium.

2. The lymphoid cell culture media according to claim 1, characterised in that the medium is a high density cell culture medium.

3. The lymphoid cell culture media according to claim 1, characterised in that the medium is a protein-free cell culture medium.

4. A medium concentrate for preparation of the lymphoid cell culture media as defined in claim 1 which is either a solid or a liquid.

5. The lymphoid cell culture media of claim 3 wherein the protein-free medium is suitable for NSO cell culture.

6. A NSO cell culture media, characterized in that the medium is serum-free and suited for culturing lymphoid cells and comprises an alkali metal salt of acetate or an alkaline earth metal salt of acetate or a metal acetate salt at a concentration of from 5 to 20 mM, said cell culture medium being free of butyrate and said alkali metal not being lithium.

7. The lymphoid cell culture media according to claim 1, wherein the alkali metal salt of acetate is sodium acetate or potassium acetate.

8. The NSO cell culture media according to claim 6, wherein the alkali metal salt of acetate is sodium acetate or potassium acetate.

9. The NSO cell culture media according to claim 6, characterised in that the medium is a high density cell culture medium.

10. The NSO cell culture media according to claim 6, characterised in that the medium is a protein-free cell culture medium.

11. A medium concentrate for preparation of the NSO cell culture media as defined in claim 6 which is either a solid or a liquid.

12. The lymphoid cell culture media of claim 1 wherein the alkali metal salt of acetate or the alkaline earth metal salt of acetate or the metal acetate salt is present at a concentration of from 5 to 15 mM.

13. The lymphoid cell culture media of claim 1 wherein the alkali metal salt of acetate or the alkaline earth metal salt of acetate or the metal acetate salt of is present at a concentration of from 5 to 12 mM.

14. The NSO cell culture media of claim 6 wherein the alkali metal salt of acetate or the alkaline earth metal salt of acetate or the metal acetate salt is present at a concentration of from 5 to 15 mM.

15. The NSO cell culture media of claim 6 wherein the alkali metal salt of acetate or the alkaline earth metal salt of acetate or the metal acetate salt is present at a concentration of from 5 to 12 mM.

* * * * *